United States Patent [19]

Tsuda et al.

[11] Patent Number: 5,994,590
[45] Date of Patent: Nov. 30, 1999

[54] PROCESS FOR PRODUCING 7-OCTEN-1-AL

[75] Inventors: Tomoyasu Tsuda, Kurashiki; Yasuo Tokitoh, Kitakanbara-gun; Kazunori Watanabe; Takashi Hori, both of Kurashiki, all of Japan

[73] Assignee: Kuraray Co., Ltd., Kurashiki, Japan

[21] Appl. No.: 09/163,006

[22] Filed: Sep. 30, 1998

[30] Foreign Application Priority Data

Sep. 30, 1997 [JP] Japan .................................. 9-266232

[51] Int. Cl.⁶ ............................ C07C 45/67; B01J 23/72
[52] U.S. Cl. .......................................... 568/450; 502/345
[58] Field of Search .................... 568/450, 873; 502/345

[56] References Cited

U.S. PATENT DOCUMENTS

| | | | |
|---|---|---|---|
| 4,463,196 | 7/1984 | Chabardes et al. | 568/450 |
| 4,510,331 | 4/1985 | Yoshimura et al. | 568/450 |

FOREIGN PATENT DOCUMENTS

| | | |
|---|---|---|
| 0 069 339 | 1/1983 | European Pat. Off. |
| 1 265 044 | 3/1972 | United Kingdom . |

OTHER PUBLICATIONS

Chemical Abstracts, vol. 114, No. 7, AN 114:61540v, Feb. 18, 1991. JP 02 218638, Aug. 31, 1990.
Chemical Abstracts, vol. 122, No. 11, AN 122;132583q, Mar. 13, 1995, JP 06 210173, Aug. 2, 1994.

*Primary Examiner*—John Kight
*Assistant Examiner*—Charanjit S. Aulakh
*Attorney, Agent, or Firm*—Oblon, Spivak, McClelland, Maier & Neustadt, P.C.

[57] ABSTRACT

A process for producing 7-octen-1-al by isomerization of 2,7.octadien-1-ol by feeding 2,7-octadien-1-ol and hydrogen to a reaction zone in the presence of a copper catalyst while controlling the molar ratio of 2,7-octadien-1-ol to hydrogen within a range of 99/1 to 75/25, and effecting isomerization in the gaseous phase. This process ensures a high yield, a high selectivity and stable operation over a long period of time.

16 Claims, No Drawings

PROCESS FOR PRODUCING 7-OCTEN-1-AL

BACKGROUND OF THE INVENTION

1. Field of the Invention

The present invention relates to a process for producing 7-octen-1-al by isomerizing 2,7-octadien-1-ol.

2. Discussion of the Background

The compound 7-octen-1-al contains a terminal double bond and an aldehyde group with high reactivity and is very useful as a starting material for various industrial chemicals.

For instance, 7-octen-1-al can be converted into 1,9-nonanedial by hydroformylation, which can give various starting materials for synthesizing polymers, such as 1,9-nonanediol, azelaic acid and 1,9-nonanediamine. Also, 7-octen-1-al can be converted to 7-octenoic acid by oxidation with oxygen in the presence of a catalyst such as a cobalt salt, a manganese salt, a nickel salt, a copper salt or an iron salt. Furthermore, 7-octen-1-al can be converted by reduction into 7-octen-1-al or 1-octanol, or can be converted to capric acid by reduction of the double bond and oxidation of the aldehyde group.

Japanese Patent Publication No. 60378/1987 and Japanese Patent Application Laid-Open No. 118535/1983 disclose a process for producing 7-octen-1-al, which comprises isomerizing 2,7-octadien-1-ol in the presence of a catalyst selected from the group consisting of copper catalysts and chromium catalysts. Japanese Patent Application Laid-Open No. 218638/1990 (Patent No. 2565561) discloses a process for producing 7-octen-1-al, which comprises isomerizing, at a temperature of 180–250° C., 2,7-octadien-1-ol in the presence of at least one compound selected from the group consisting of n-octanol, 3-octanol and 7-octen-1-ol in an amount of 50–200% by weight based on the weight of 2,7-octadien-1-ol using a metal oxide catalyst containing at least two metals selected from the group consisting of copper, chromium and zinc.

In the process described in Japanese Patent Publication No. 60378/1987 and Japanese Patent Application Laid-Open No. 118535/1983, there is inevitably produced as a byproduct, 2,7-octadien-1-al which it is difficult to separate by distillation from the product 7-octen-1-al. The byproduct 2,7-octadien-1-al, is a catalyst poison for hydroformylation and decreases the yield of 1,9-nonanedial on hydroformylation of the obtained 7-octen-1-al. This fact is clear from the description in Japanese Patent Application Laid-Open No. 218638/1990 that when the reaction is conducted in accordance with the procedure given in the Examples of Japanese Patent Publication No. 60378/1987 with repeated use of the same catalyst, there occurs a gradual increase of 2,7-octadien-1-al. The process described in Japanese Patent Application Laid-Open No. 218638/1990 decreases the amount of 2,7-octadien-1-al byproduct to a low level. Example 2 shows a level of only 0.7%, which is the largest figure in the Examples after a 7-hour reaction. However, with this process, n-octanol and 3-octanol, which are used as sources for generating hydrogen, are necessarily converted by dehydrogenation during the reaction, into n-octylaldehyde (boiling point: 173° C./760 mmHg) and 3-octanone (boiling point; 168° C./760 mmHg) respectively, each having a boiling point very close to that (174° C./760 mmHg) of 7-octen-1 al. As a result, the process described in Japanese Patent Application Laid-Open No. 218638/1990 is deficient since it is very difficult to separate the desired product from these byproducts by distillation.

In order to solve the above problem of the process described in Japanese Patent Application Laid-Open No. 218638/1990, it is necessary to develop a process which does not use n-octanol, 3-octanol or 7-octen-1-ol. The present inventors have, therefore, studied in detail the mechanism of formation of 7-octen-1-al from 2,7-octadien-1-ol. They discovered that the reaction is a formal isomerization which comprises dehydrogenation of the allyl alcohol part of 2,7-octadien-1-ol to form 2,7-octadien-1-al and the succeeding hydrogenation of the carbon-carbon double bond conjugating with the aldehyde group to form 7-octen-1-al. Thus, the production of 2,7-octadien-1-al in this reaction is due to the fact that hydrogen formed by dehydrogenation is consumed not only for hydrogenation to form 7-octen-1-al, but also for the formation of various byproducts, thereby causing a part of the intermediate product 2,7-octadien-1-al to remain in the reaction zone. Indeed, the present inventors conducted isomerization in accordance with the procedures given in Comparative Examples 1, 3, 4 and 5 in the instant specification to confirm that 2,7-octadien-1-al was produced in large amounts. The present inventors also discovered that isomerization over a long period of time, as shown in Comparative Example 6 of the instant specification resulted in an increase in the amount of 2,7-octadien-1-al product and, at the same time, a decrease in the conversion of 2,7-octadiene-1-ol, so that the selectivity to 7-octen-1-al decreases. In summary, a serious problem was found in that 2,7-octadien-1-al decreased the catalytic activity for the isomerization.

Furthermore, when the reaction is conducted by a reaction-distillation method, which is a particularly referred embodiment in Japanese Patent Publication No. 60378/1987, Japanese Patent Application Laid-Open No. 118535/1983 and Japanese Patent Application Laid-Open No. 218638/1990, another problem occurs since high-boiling byproducts inevitably result originating from the aldehydes formed by the reaction, and this leads to a decrease in the yield.

It is, therefore, important, if the reaction is to be conducted over a period of time, to suppress the formation of 2,7-octadien-1-al (which decreases the catalytic activity) and the production of high-boiling byproducts. As described above, the mechanism involved in the formation of 7-octen-1-al from 2,7-octadien-1-ol is a formal isomerization which involves dehydrogenation of the allyl alcohol part of 2,7-octadien-1-ol to form 2,7-octadien-1-al and the hydrogenation of the carbon-carbon double bond conjugating with the aldehyde group to form 7-octadien-1-al. The byproduction of 2,7-octadien-1-al is a result of the fact that the hydrogen formed on dehydrogenation is consumed not only for hydrogenation to 7-octen-1-al, but for various side reactions. This leads to insufficient hydrogenation of 2,7-octadion-1-al and thus allows this aldehyde to remain in the reaction zone. Since hydrogenation of the remaining 2,7-octadien-1-al by adding hydrogen (which is inexpensive) to the reaction zone would reduce the content of 2,7-octadien-1-al in the final reaction mixture, the inventors decided to study the hydrogenation conditions in detail. The specification of Japanese Patent Publication No. 60378/1987 states: "The isomerization reaction is preferably carried out in an atmosphere of a gas which is inert under the reaction condition. The whole or part of the inert gas may be replaced with hydrogen gas. When the reaction is carried out in the co-presence of hydrogen, the hydrogen partial pressure is preferably kept below 10 atmospheres. At a hydrogen partial pressure exceeding 10 atmospheres, the hydrogenation reaction prevails, unfavorably causing decrease in the selectivity toward 7-octen-1-al." and the same description is disclosed in the specification of Japanese Patent Application Laid- Open No. 118535/1983. However, the specification of Japanese Patent Publication No. 60378/1987 only discloses in its Examples 2 and 4, that the ratios of isomerization to produce 7-octen-1-al under a hydrogen atmosphere were 43% and 73%, respectively, and gives no description of the amount of hydrogen added. The specification of Japanese Patent Application Laid-Open No. 118585/1983 discloses in its Examples 4 and 6 the results that the selectivity toward 7-octen-1-al production under the flow of hydrogen gas were 92% and 79%, respectively. The present inventors have studied this reaction and found the selectivity toward 7-octen-1-al production is low, that is, the byproduction of other hydrogenation products prevails in this reaction, and the activity of the catalyst decreases as the reaction proceeds. This is shown in Comparative Example 7 of the specification. The catalysts disclosed in these prior art citations are known catalysts for hydrogenation. It would be expected, therefore, that addition of hydrogen to the reaction zone would cause various hydrogenation side reactions to occur and, in some cases, further hydrogenation of 7-octen-1-al thereby decreasing the reaction selectivity to 7-octen-1-al. However, the prior art contains no suggestion of the effect of the addition of hydrogen to suppress byproduction of 2,7-octadien-1-al.

SUMMARY OF THE INVENTION

It is, therefore, an object of the present invention to provide a process for producing 7-octen-1-al in high yields without adversely affecting catalytic activity and without the adverse production of byproducts.

As a result of extensive study, the present inventors have surprisingly discovered that by conducting the isomerization reaction in the presence of a copper catalyst and controlling the ratio of 2,7-octadien-1-ol and hydrogen, it is possible to suppress the byproduction of 2,7-octadien-1-al without decreasing the production of 7-octen-1-al and further, that conducting the reaction in the gaseous phase facilitates the rapid removal of the product from the reaction zone and suppresses formation of high-boiling byproducts such that a stable reaction is possible when conducted over a long period of time.

The present invention provides a process for producing 7-octen-1-al by isomerization of 2,7-octadien-1-ol which comprises feeding 2,7-octadien-1-ol and hydrogen to a reaction zone in the presence of a copper catalyst, while controlling the molar ratio of 2,7-octadien-1-ol to hydrogen within a range of 99/1 to 75/25, and effecting isomerization in the gaseous phase.

DETAILED DESCRIPTION OF THE PREFERRED EMBODIMENTS

In the present invention, the amount of hydrogen to be fed together with 2,7-octadien-1-ol is within a molar range of about 99/1 to 75/25 which corresponds to 1–25 mol % of hydrogen in the mixture of 2,7-octadien-1-ol and hydrogen. The molar ratio of 2,7-octadien-1-ol to hydrogen is preferably within a range of about 97/3 to 80/20. If less than about 1 mol % of hydrogen is present in the mixture of the two components, the suppression of 2,7-octadien-1-al byproduct will be insufficient. On the other hand, use of hydrogen in an amount exceeding about 25 mol % will adversely effect the selectivity of the reaction to 7-octen-1-al.

Examples of the copper catalyst used in the process of the invention include reduced copper, Raney copper, copper-zinc oxide, copper-chromium oxide, copper aluminum oxide, copper-iron-aluminum oxide, copper-zinc-aluminum oxide and copper-zinc-titanium oxide and mixtures thereof. These catalysts are commercially available but can also be prepared in accordance with the processes described in, for example, Shokubai Kogaku Koza 10; List of Element-Based Catalysts 365–367 issued on Feb. 25, 1967 from Chijin Shokan Co., Ltd. The catalysts may be partially modified with other metals such as tungsten, molybdenum, rhenium, zirconium, manganese, titanium, barium or the like. The catalysts may also be used on a carrier such as alumina, silica or diatomaceous earth. The catalysts may have their surfaces pretreated with an alkali metal and/or an alkali earth metal. They may be used singly or in combination of 2 or more.

It is desirable to activate the catalyst by treating with hydrogen before use, which ensures higher catalytic activity.

In the process of the present invention, 2,7-octadien-1-ol and hydrogen may be fed together with a primary or secondary alcohol represented by the general formula (I):

$$R^1R^2CH\text{—}OH \qquad (I)$$

wherein $R^1$ and $R^2$ each represents a hydrogen atom, or an alkyl, alkenyl, aryl or cycloalkyl group which may be substituted; or $R^1$ and $R^2$ together represent a cycloalkyl group which may be substituted.

Preferably, $R^1$ and $R^2$ in the formula (1) each represents a hydrogen atom, a linear or branched alkyl having 1–10 carbon atoms, or an alkenyl, aryl or cycloalkyl group which may be substituted with a lower alkyl group having 1–8 carbon atoms or phenyl group; or $R^1$ and $R^2$ together represent a cycloalkyl group which may be substituted with a lower alkyl group having 1–3 carbon group.

Examples of the primary or secondary alcohol which may be used in the present invention are saturated primary alcohols, e.g. methanol, ethanol, n-propanol, n-butanol, isobutyl alcohol, n-pentanol, isopentyl alcohol, 2-methyl-1-butanol, neopentyl alcohol, n-hexanol, 2-methyl-1-pentanol, 2-ethyl-1-butanol, n-heptanol, n-octanol, 2-ethyl-1-hexanol, n-nonanol, 3,5,5-trimethyl-1-hexanol and n-decanol; unsaturated primary alcohols, e.g. allyl alcohol, methallyl alcohol, crotyl alcohol, 4-penten-1-ol, 3-methyl-3-buten-1-ol, 3-methyl-2-buten-1-ol, 5-hexen-1-ol and 7-octen-1-ol; aralkyl primary alcohols, e.g. benzyl alcohol; linear secondary alcohol, e.g. 2-propanol, 2-butanol, 2-pentanol, 3-pentanol, 4-methyl-2-pentanol, 2-heptanol, 2-octanol, 3-octanol and diisobutylcarbinol; and cyclic secondary alcohols, e.g. cyclopentanol, cyclohexanol and methylcyclohexanol. These alcohols may be used singly or in combination of 2 or more.

The process of the present invention can be carried out under atmospheric pressure, under a higher pressure or under a reduced pressure. As the reaction apparatus, a conventional fixed bed flow-system reaction apparatus can be used. Use of the flow-system reaction facilitates rapid removal of the product from the reaction zone, thereby suppressing formation of high boiling byproducts from aldehyde group-containing compounds.

In carrying out the process of the present invention, it may be desirable to use an inert carrier gas but the use of such a carrier gas is not essential. Thus, 2,7-octadion-1-ol may be simply mixed with hydrogen and, if desired, a primary or secondary alcohol and the obtained mixture may be used as the gaseous starting material. Nitrogen is advantageously used as the inert carrier gas in the process of the present invention.

The reaction temperature is preferably in a range of about 100 to about 260° C., more preferably in a range of about 160 to about 240° C. At a temperature lower than 100° C., the reaction tends to proceed very slowly. On the other hand, at a temperature above 260° C., sintering of the catalyst may occur and the catalyst may be degraded with metallic copper precipitating on the surface, thereby decreasing both the selectivity and the catalyst life.

The process of the present invention can be carried out over a wide range of the liquid hourly space velocity (LHSV) of 2,7-octadien-1-ol. The preferred range of LHSV is from about 0.01–20 $hr^{-1}$, with a range of about 0.5–10 $hr^{-1}$ more preferred. An LHSV of less than about 0.01 $hr^{-1}$ may lead to a low productivity of 7-octen-1-al and the process, therefore, cannot be used on a commercial scale. On the other hand, an LHSV exceeding about 20 $hr^{-1}$ may decrease the conversion of 2, 7 octadien-1-ol.

The 7-octen-1-al that forms in the reaction can be separated from the reaction mixture by conventional distillation.

Other features of the invention will become apparent in the course of the following detailed descriptions of exemplary embodiments which are given for illustration of the invention and are not intended to be limiting thereof. In the Examples and Comparative Examples that follow, the following abbreviations are used.

GHSV: gas hourly space velocity ($hr^{-1}$); defined as:

[Volume per hour of feed gas passing the total volume of catalyst]/[total volume of catalyst]

LHSV: liquid hourly space velocity ($hr^{-1}$); defined as:

[Volume per hour of feed liquid passing the total volume of catalyst]/[total volume of catalyst]

The following describes the apparatus, quantitative analysis, catalyst activation treatment and reaction procedures employed in the Examples.

Reaction Apparatus

A quartz glass tube having an inner diameter of 24 mm and a total length of 720 mm and equipped in its inside with a thermometer sheath tube was packed with 25 ml of a copper catalyst. The catalysts used were all molded pellets and had a length of catalyst layer of about 65 mm. The bottom part of the tube beneath the catalyst layer was packed with glass beads having an average particle diameter of 5 mm, and on the top thereof the same glass beads were packed to a height of about 150 mm, which constituted a pre-heating zone. The catalyst and glass beads portions were heated in a cylindrical electric oven and the temperature of the catalyst layer, which was the reaction temperature, was measured and adjusted to a prescribed temperature. The bottom part of the reaction tube was fitted with a cooling device, sampler, reservoir and cold trap, so that the distilled reaction mixture was recoverable. A metering feed pump was used to feed 2,7-octadien-1-ol at a prescribed rate and a gas mixer capable of adjusting the composition and flow rate was used to feed nitrogen and hydrogen.

Analysis of reaction mixture

The distillate was sampled at a prescribed interval and subjected to gas chromatography by using capillary columns (DB-WAX, 30 m, diameter: 0.25 mm, film: 0.25 μm) made by J & W Scientific Company and with Triglyme as an internal standard substance.

Analytical conditions

Injection temperature and detection temperature: 280° C.

Temperature elevation program: 100° C. (kept for 2 minutes) →60° C./min→240° C. (kept for 5 minutes)

Activation of catalyst by treating with hydrogen

After the inside of the reaction apparatus packed with the catalyst had been sufficiently replaced by nitrogen, the catalyst layer was gradually heated while nitrogen was fed at GHSV=300 $hr^{-1}$. After the temperature of the catalyst layer had exceeded 120° C., a nitrogen/hydrogen mixed gas containing 3% of hydrogen was introduced. The mixing ratio of hydrogen was gradually increased, while care was taken to keep the catalyst layer temperature from exceeding 220° C. to prevent vigorous heat generation. When heat generation was no longer observed, the temperature of the catalyst layer was maintained at 200–220° C. for 4–5 hours, while only hydrogen was fed at GHSV=300 $hr^{-1}$.

Reaction Procedure

After the activation treatment of the catalyst, the temperature of the reaction layer was adjusted to about 20° C. lower than the intended reaction temperature, while hydrogen was continuously introduced. The feed gas was then changed to a mixed gas having a prescribed nitrogen/hydrogen ratio, which was fed at a prescribed GHSV. Thereafter, 2,7-octadien-1-ol was fed at a prescribed LHSV and the heating was adjusted to achieve the desired temperature. While the reaction temperature was kept constant, the distillate was sampled at a prescribed time and subjected to analysis.

EXAMPLES 1 THROUGH 5 AND COMPARATIVE EXAMPLES 1 THROUGH 5

Reactions were carried out with various copper catalysts, while the LHSV of 2,7-octadien-1-ol was set at 1.5 $hr^{-1}$ and with various reaction temperatures and compositions of mixed nitrogen/hydrogen gases. Table 1 shows the compositions of the copper catalysts used and Table 2 the reaction results after 2-hour reaction.

TABLE 1

| Copper Catalyst Used (all made by Nikki-Kagaku Co., Ltd.) | | | | |
|---|---|---|---|---|
| Code | Composition (% by weight) | | | |
| N202D | CuO: 38.5 | $Cr_2O_3$: 35.6 | $MnO_2$: 2.0 | |
| N202E | CuO: 39.8 | $Cr_2O_3$: 41.1 | $NnO_2$: 1.9 | BaO: 1.7 |
| E26L | Cu: 23.7 | Fe: 20.9 | Al: 18.6 | Zn: 1.3 |
| N211 | CuO: 49.0 | ZnO: 43.6 | | |

Average diameter of pellets:
φ 5 × 5 (N202D, N202E, E26L)
φ 6 × 6 (N211)

TABLE 2

| | Catalyst | $N_2/H_2$ (vol) | $ODA/H_2$ molar ratio | Temp. (° C.) | Conv. of ODA (%) | Selectively (%) to | | | | | | |
|---|---|---|---|---|---|---|---|---|---|---|---|---|
| | | | | | | OD | OL | 7-OEL | ODL | OA | 7-OEA | H.B. |
| Ex. 1 | N202D | 95/5 | 90.5/9.5 | 240 | 97.1 | 3.0 | 13.0 | 71.4 | 3.6 | 1.2 | 6.4 | 0.6 |
| Ex. 2 | N202D | 90/10 | 82.7/17.3 | 240 | 96.8 | 3.1 | 11.7 | 68.9 | 2.2 | 1.9 | 11.6 | 0.4 |
| Ex. 3 | E26L | 95/5 | 90.5/9.5 | 200 | 95.3 | 2.5 | 2.9 | 78.5 | 5.0 | 0.3 | 8.7 | 1.3 |
| Ex. 4 | N211 | 95/5 | 90.5/9.5 | 240 | 85.4 | 2.0 | 6.7 | 67.6 | 6.9 | 1.1 | 10.2 | 4.7 |

TABLE 2-continued

| | Catalyst | $N_2/H_2$ (vol) | $ODA/H_2$ molar ratio | Temp. (°C.) | Conv. of ODA (%) | Selectively (%) to | | | | | | |
|---|---|---|---|---|---|---|---|---|---|---|---|---|
| | | | | | | OD | OL | 7-OEL | ODL | OA | 7-OEA | H.B. |
| Ex. 5 | N202E | 90/10 | 82.7/17.3 | 240 | 94.3 | 4.1 | 12.5 | 63.5 | 3.6 | 1.4 | 7.5 | 6.2 |
| Comp. Ex. 1 | N202D | 100/0 | — | 240 | 86.4 | 1.6 | 7.4 | 70.2 | 12.5 | 0.5 | 4.7 | 0.7 |
| Comp. Ex. 2 | N202D | 80/20 | 70.7/29.3 | 240 | 97.4 | 3.7 | 9.4 | 58.6 | 1.1 | 3.2 | 19.3 | 1.8 |
| Comp. Ex. 3 | N202E | 100/0 | — | 240 | 74.0 | 2.4 | 7.2 | 52.6 | 13.9 | 0.6 | 5.3 | 13.9 |
| Comp. Ex. 4 | E26L | 100/0 | — | 200 | 93.8 | 2.4 | 4.8 | 77.2 | 9.8 | 0.2 | 4.0 | 1.0 |
| Comp. Ex. 5 | N211 | 100/0 | — | 240 | 87.1 | 1.7 | 5.4 | 67.9 | 11.5 | 0.6 | 5.9 | 5.6 |

GHSV: 480 ($hr^{-1}$), LHSV of ODA: 1.5 ($hr^{-1}$)
Coding
OD: octadienes, ODA: 2.7-octadien-1-ol, OL: 1-octanal, 7-OEL: 7-octen-1-al, ODL; 2,7-octadien-1-al, 7-OEA: 7-octen-1-ol, OA: 1-octanol, H.B.: high-boiling compounds.

The results of Examples 1 through 5 and Comparative Examples 1 through 5 clearly show that in the production of 7-octen-1-al with various copper catalysts, the presence of hydrogen reduces the amount of 2,7-octadien-1-al byproduct. It is also clear from the results of Comparative Example 2 that an amount of hydrogen exceeding the range specified reduces the selectivity toward the production of the desired 7-octen-1-al.

EXAMPLE 6

Reaction was carried out with a catalyst of copper-iron-aluminum catalyst (E26L; made by Nikki Kagaku Co., Ltd.) at a reaction temperature of 220° C. by feeding 2,7-octadien-1-ol at an LHSV of 1.5 $hr^{-1}$ and a 95/5 by volume nitrogen/hydrogen mixed gas at a GHSV of 480 $hr^{-1}$. The above volume ratio corresponds to a molar ratio of 2,7-octadien-1-ol to hydrogen of 90.5/9.5. The reaction time and reaction results are shown in Table 3. It is seen that excellent results were obtained even after 200 hours of continuous reaction operation.

TABLE 3

| Reaction time (hr) | Conversion of 2,7-octadien-1-ol (%) | Selectivity to | |
|---|---|---|---|
| | | 7-octen-1-al (%) | 2,7-octadien-1-al (%) |
| 5 | 99.0 | 76.8 | 3.3 |
| 50 | 95.8 | 78.2 | 3.1 |
| 100 | 96.1 | 77.4 | 3.3 |
| 200 | 95.5 | 76.7 | 3.7 |

COMPARATIVE EXAMPLE 6

Reaction was carried out with a copper-iron-aluminum catalyst (E26L; made by Nikki Kagaku Co., Ltd.) at a reaction temperature of 220° C. by feeding 2,7-octadien-1-ol at an LHSV of 1.5 $hr^{-1}$ and nitrogen gas at a GHSV of 480 $hr^{-1}$. The reaction results with time are shown in Table 4. It is seen that the conditions employed here without hydrogen led to a significant production of 2, 7-octadien-1-al byproduct and a decrease in both conversion and selectivity.

TABLE 4

| Reaction time (hr) | Conversion of 2,7-octadien-1-ol (%) | Selectivity to | |
|---|---|---|---|
| | | 7-octen-1-al (%) | 2,7-octadien-1-al (%) |
| 5 | 93.6 | 76.0 | 10.0 |
| 50 | 87.5 | 73.6 | 11.5 |
| 100 | 76.6 | 72.2 | 13.1 |

EXAMPLE 7

Reaction was carried out with a copper-iron-aluminum catalyst (E26L) at a reaction temperature of 220° C. by feeding a 90/10 mol ratio of 2,7-octadien-1-ol/7-octen-1-ol mixed gas at an LHSV of 1.7 $hr^{-1}$ and a 98/2 ratio by volume nitrogen/hydrogen mixed gas at a GHSV of 480 $hr^{-1}$. The above volume ratios correspond to a molar ratio of 2,7-octadien-1-ol to hydrogen of 96/4. The reaction results over time are shown in Table 5. It is seen that no change occurred in catalytic activity even after an elapsed time of 100 hours.

TABLE 5

| Reaction time (hr) | Conversion of 2,7-octadien-1-ol (%) | Selectivity to | |
|---|---|---|---|
| | | 7-octen-1-al (%) | 2,7-octadien-1-al (%) |
| 5 | 98.7 | 85.6 | 0.6 |
| 50 | 99.0 | 85.2 | 0.7 |
| 100 | 98.5 | 85.1 | 0.8 |

COMPARATIVE EXAMPLE 7

A 100-ml three-necked flask, connected to a distillation apparatus, equipped with an electromagnetic stirrer, an inlet for liquid and an another inlet for gas, was charged with 30 ml of 2,7.octadien-1-ol and 2.0 g of Raney-copper(made by Kawaken Fine Chemical Co., Ltd.) and was immersed in an oil-bath, whose temperature was maintained at 205° C. While vigorously stirring the mixture in this flask, hydrogen gas was introduced at a rate of 30 1/hr, and 2,7.octadien-1-ol was continuously introduced at the rate of 170 ml/hr. Distillate was collected at the rate of 170 ml/hr while the volume of the content in the reaction flask was controlled to maintain about 30 ml therein. After starting the reaction, the distillate was periodically analyzed by the method described above. The results are shown in Table 6. It is seen that as the reaction proceeds the selectivity toward production of 7-octen-1-al is lower and the activity of the catalyst decreases.

TABLE 6

| Reaction time (hr) | Conversion of 2,7-octadien-1-ol (%) | Selectivity to | |
|---|---|---|---|
| | | 7-octen-1-al (%) | 2,7-octadien-1-al (%) |
| 5 | 93.1 | 9.1 | 0.2 |
| 10 | 86.8 | 8.9 | 0.5 |
| 20 | 59.2 | 8.5 | 1.1 |

In Tables 2 through 6, the selectivities were calculated based on the starting material ODA.

The following is a flow-sheet diagram designed to facilitate an understanding of the invention as discussed in the above description and Examples.

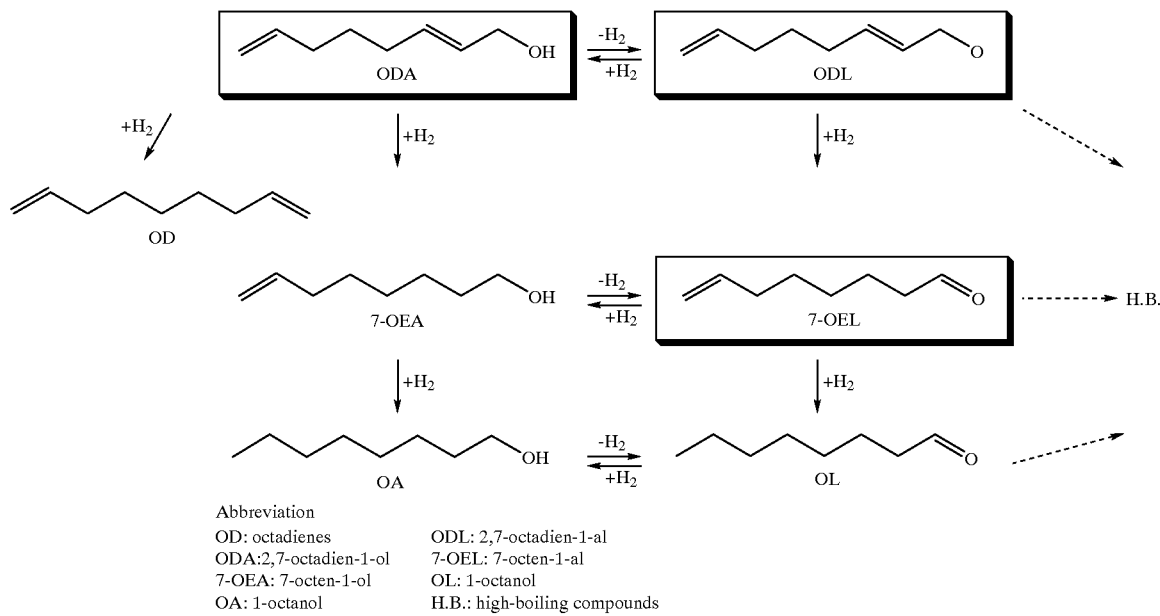

Abbreviation
OD: octadienes
ODA: 2,7-octadien-1-ol
7-OEA: 7-octen-1-ol
OA: 1-octanol
ODL: 2,7-octadien-1-al
7-OEL: 7-octen-1-al
OL: 1-octanol
H.B.: high-boiling compounds Obviously, numerous variations and modifications of the invention are possible in light of the above teachings. It is, therefore, to be understood that within the scope of the appended claims, the invention may be practiced otherwise than as specifically described herein.

This application is based on Japanese Patent Application No. 266232/1997, filed Sep. 30, 1997, the entire disclosure of which is incorporated herein by reference.

What is claimed as new and is intended to be secured by Letters Patent is:

1. A process for producing 7-octen-1-al by isomerization of 2,7-octadien-1-ol which comprises introducing a mixture of 2,7-octadien-1-ol and hydrogen into a reaction zone in the presence of a copper catalyst, the molar ratio of 2,7-octadien-1-ol to hydrogen being within a range of about 99/1 to about 75/25 and heating in the gaseous phase to effect isomerization.

2. The process according to claim 1 wherein the molar ratio of 2,7-octadien-1-ol to hydrogen is within a range of about 97/3 to about 80/20.

3. The process according to claim 1 wherein the 2,7-octadien-1-ol and hydrogen are introduced into the reaction zone while mixed with an inert carrier gas.

4. The process according to claim 3 wherein the inert carrier gas is nitrogen.

5. The process according to claim 1 wherein the isomerization is conducted at a temperature within a range of about 100–260° C.

6. The process according to claim 5 wherein the isomerization is conducted at a temperature in the range of about 160 to about 240° C.

7. The process according to claim 1 wherein the 2,7-octadien-1-ol is introduced into the reaction zone at a liquid hourly space velocity of about 0.01 to about 20 $hr^{-1}$.

8. The process according to claim 7 wherein the 2,7-octadien-1-ol is introduced into the reaction zone at a liquid hourly space velocity of about 0.5 to about 10 $hr^{-1}$.

9. The process of claim 1 wherein the copper catalyst is selected from the group consisting of reduced copper, Raney copper, copper-zinc oxide, copper-chromium oxide, copper-aluminum oxide, copper-iron-aluminum oxide, copper-zinc-aluminum oxide, copper-zinc-titanium oxide and mixtures thereof.

10. A process as in claim 9 wherein the copper catalyst is further modified with at least one metal selected from the group consisting of tungsten, molybdenum, rhenium, zirconium, manganese, titanium, and barium.

11. The process as in claim 1 wherein the copper catalyst is in a form carried on a carrier.

12. A process as in claim 1 wherein the copper catalyst has been preactivated by contact with hydrogen.

13. A process as in claim 1 wherein a primary or secondary alcohol is introduced into the reaction zone.

14. A process as in claim 13 wherein the alcohol is of the formula $R^1R^2CH$—OH wherein $R^1$ and $R^2$ each represents a hydrogen atom or an alkyl, alkenyl, aryl or cycloalkyl group which may be substituted or $R^1$ and $R^2$ together represent a cycloalkyl group which may be substituted.

15. A process as set forth in claim 14 where $R^1$ and $R^2$ represent hydrogen, a linear or branched alkyl group having 1–10 carbon atoms, or an alkenyl, aryl or cycloalkyl group which may be substituted with a lower alkyl group having 1–8 carbon atoms or a phenyl group or $R^1$ and $R^2$ together represent a cycloalkyl group which may be substituted with a lower alkyl group of 1–3 carbon atoms.

16. A process as in claim 1 wherein the isomerization is conducted in a fixed bed flow system.

* * * * *